United States Patent [19]

Bade

[11] Patent Number: 4,861,517

[45] Date of Patent: Aug. 29, 1989

[54] METHOD FOR THE PREPARATION OF CONCENTRATED FLOWABLE AQUEOUS SOLUTIONS OF BETAINES: ADDITION OF MINERAL ACID

[75] Inventor: Volkbert Bade, Essen, Fed. Rep. of Germany

[73] Assignee: Th. Goldschmidt AG

[21] Appl. No.: 223,286

[22] Filed: Jul. 22, 1988

[30] Foreign Application Priority Data

Aug. 7, 1987 [DE] Fed. Rep. of Germany ....... 3726322

[51] Int. Cl.$^4$ .................... A61K 7/07; B01F 17/18; C07C 103/54; C11D 1/90
[52] U.S. Cl. .................... 252/546; 252/142; 252/527; 252/547; 252/DIG. 5; 252/DIG. 13
[58] Field of Search ............. 252/546, 547, 142, 527

[56] References Cited

U.S. PATENT DOCUMENTS

| 3,225,074 | 12/1965 | Cowen et al. | 252/8.75 |
| 4,076,743 | 2/1978 | Koch et al. | 252/8.55 |
| 4,148,762 | 4/1979 | Koch et al. | 252/544 |

FOREIGN PATENT DOCUMENTS 3613944  8/1987  Fed. Rep. of Germany .

*Primary Examiner*—A. Lionel Clingman
*Attorney, Agent, or Firm*—Toren, McGeady & Associates

[57] ABSTRACT

A method is disclosed for the preparation of flowable aqueous solutions of betaines of the general formula

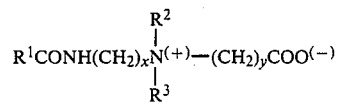

wherein
- $R^1$ is the alkyl portion of a fatty acid with 6 to 18 carbon atoms,
- $R^2$, $R^3$ are the same or different and represent alkyl groups with 1 to 4 carbon atoms
- $x$ is 2 or 3 and
- $y$ is 1, 2 or 3 by quaternization of the fatty acid amide $R^1CONH(CH_2)_xNR^2R^3$ with ω-halogenalkylcarboxylic acids $X(CH_2)COOY$ or their salts (X=halogen, Y=a hydrogen, alkali or ammonium ion) in aqueous solution at elevated temperatures. The preferably still hot solution, obtained pursuant to the invention after the reaction, is brought to the desired concentration, if necessary, by the evaporation of water. Before or after the concentration of the solution is adjusted to the desired value, mineral acid is added in such amounts, that the pH of the solution becomes 1 to 4.5. If hydrogenated coconut fatty acids are used as the fatty acid mixture for the preparation of the betaine, it is possible to prepare flowable solutions with a solids content of about 54% by weight. Water-soluble nonionic surfactants may be added to the betaine solution.

14 Claims, No Drawings

METHOD FOR THE PREPARATION OF CONCENTRATED FLOWABLE AQUEOUS SOLUTIONS OF BETAINES: ADDITION OF MINERAL ACID

FIELD OF THE INVENTION

The invention generally is directed to a method for the preparation of flowable aqueous solutions of betaines of the general formula

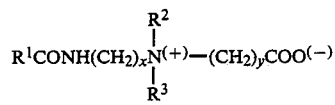

wherein
$R^1$ is the alkyl portion of a fatty acid with 6 to 18 carbon atoms,
$R^2$, $R^3$ are the same or different and represent alkyl groups with 1 to 4 carbon atoms
x is 2 or 3 and
y is 1, 2 or 3
by quaternization of the fatty acid amides

     II with ω-halogenalkylcarboxylic acids $X(CH_2)_yCOOY$ or their salts (X=halogen, Y=a hydrogen, alkali or ammonium ion) in aqueous solution at elevated temperatures.

More particularly, the invention is concerned with the preparation of flowable betaine solutions with a solids content of 43 to about 65% by weight and ab etaine content of 37 to about 55% by weight.

In a particularly preferred aspect, the invention is directed to the preparation of flowable betaine solutions of the aforementioned concentrations, which are homogeneous and have high cold stability.

BACKGROUND INFORMATION AND PRIOR ART

In recent years, betaines of formula I have gained increasing importance for the preparation of cleansing agents for the body. they combine outstanding cleansing properties with good skin compmatibility. In aqueous solution, the betaines form a stable, dense foam, which does not collapse even in the presence of soap.

The synthesis of these betaines is described in many patents, of which U.S. Pat. No. 3,225,074 is cited as representative. In general, the appropriate tertiary fatty acid amidamine of the general formula II is reacted with the alkali salt of an ω-halogencarboxylic acid, usually the sodium salt of chloroaceic acid. The reaction takes place in the aqueous medium. The alkali chloride, formed during the reaction, generally is not removed from the solution.

The betaines of the state of the art are most marketed in the form of their 30% by weight aqueous solutions. There has been no lack of attempts to produce more concentrated betaine solutions in order to lessen the costs of transport and storage. However, if water is withdrawn from the betaine solutions obtained according to the state of the art, the viscosity of the solutions increases rapidly. Solutions of betaines based on hydrogenated coconut fatty acid become pasty when they contain about 35 to 37% by weight of betaine and solidify on further dehydration. The concentration, above which the betaine solutions no longer are flowable, is affected by the number of carbon atoms of the fatty acid $R^1COOH$. The longer the chain length of the fatty acid or of the fatty acids of the mixture used to prepare the betaine, the more rapidly does the viscosity of the betaine solutions increase as the concentration increases. Unsaturated fatty acids with the same number of carbon atoms result in betaine solutions of lower viscosity.

Those skilled in the art know that the viscosity of an aqueous surfactant solution also increases as the concentration is increased. Frequently, however, it turns out that, when a concentration of about 60 to 70% by weight is exceeded, the viscosity at first falls off to a minimum as the concentration is increased further, only to then increase once again strongly. To explain this viscosity anomaly, it is assumed that a G phase with lamellar structure is formed in the solution (Soap, Perfumery, Cosmetics, 1982, pages 507 to 509). However, such a behavior could not be observed with betaines. On further removal of water, the solidified products do not liquefy once again.

In the German Offenlegungsschrift No. P 36 13 944.0-42, a method is described for the preparation of a flowable and pumpable solution containing at least 70% by weight of betaine of formula I, in which (a) the ammonium salt is used as salt of the halogenated carboxylic acid, (b) the quaternization is carried out in a polar organic solvent, which must not contain more than 20% by weight of water, (c) after the quaternization, any water contained is distilledc off azeotropically and the precipitated ammonium halide is removed, after which (d) the solvent is distilled off partly or completely and (e) before, simultaneously with or after the distillation, the concentration of the betaine in the solvent or solvent mixture desired for the particular application is adjusted to the desired value.

For this method then, the quaternization must be carried out in a polar organic solvent. The concentrated solution of the betaine, as product of the process, is present in a solution in a solvent or solvent mixture, which is required for the particular application.

However, there continues to be a need for producing aqueous solutions of betaines of formula I in the highest possible concentrations which in spite of their comparatively high concentration are flowwable and pumpable and, preferably, free of solvents other than water. A low viscosity of the aqueous solutions is required especially so as to be able to convey and meter the aqueous betaine solutions during further processing. There is, moreover, an appreciable economic interest in lowering the packaging, transport and storage costs and in reducing the handling expenses. It is of particular importance that the concentrated aqueous solutions can be dispersed in water duirng dilution without forming a gel.

OBJECT OF THE INVENTION

Accordingly, it is the primary object of the invention to provide a simple and economic method of preparing concentrated, flowable, aqueous betaine solutions of the indicated kind that overcome the disadvantages and drawbacks of the prior art processes.

Generally, it is an object of the invention to improve on the art of preparing betaine solutions as presently practiced.

SUMMARY OF THE INVENTION

Surprisingly, it has now been ascertained that flowable solutions of betaines of the general formula I can be prepared by quaternizing fatty acid amides $R^1CONH(CH_2)xNR^2R^3$ with ω-halogenalkylcarboxylic acids $X(CH_2)_yCOOY$ or their salts (X=halogen, Y=hydrogen, alkali or ammonium ion) in aqueous solution at elevated temperatures, by adjusting the preferably still hot solution obtained after the reaction, if necessary by evaporation of water, to the desired concentration and, before or after adjusting the concentration of the solution to the desired value, adding mineral acid to the solution in such amounts, that the pH of the solution is 1 to 4.5.

As mineral acid, preferably hydrochloric, sulfuric or phosphoric acid is used.

The addition of the mineral acid takes place after the quaternization reaction. If the solution initially obtained is to be concentrated, if necessary, by evaporation under reduced pressure, the mineral acid is preferably added before the evaporation, in order to avoid the formation of highly viscous solutions. It is, however, entirely possible to add the mineral acid to the concentrated gelatinous solution, which liquefies on being mixed with the mineral acid.

The quaternization reaction can be carried out by known methods. The alkali salt, preferably the sodium salt of monochloracetic acid, is added to the fatty acid amidamine of formula II in an aqueous medium. The quaternization reaction is allowed to proceed at temperatures ranging from about 80° C. to the relfuxing temperature of the reaction mixture. It is, however, also possible first to dissolve the monochloroacetic acid in water and to stir a melt of the fatty acid amidamine of formula II into the solution. An exothermic reaction takes place. When this has subsided, the amount of alkali solution required for neutralization is added slowly. The latter method (acid method) makes it possible to prepare solutions with a somewhat higher concentration but the same viscosity.

If a fatty acid mixture obtained from hydrogenated coconut fat is used for the synthesis of the fatty acid amidamine of formula I, the methods of the state of the art produce betaine solutions, which are still flowable up to the concentration (in % by weight) as indicated hereinafter. Above this concentration, however, they gel or solidify and can then no longer be handled.

STATE OF THE ART (COMPARISON)

| Quaternization with | Solids Content | Betaine Content |
| --- | --- | --- |
| ClCH$_2$COONa | 42 | 36 |
| ClCH$_2$COOH/NaOH (acid method) | 44 | 38 |
| ClCH$_2$COOH/KOH (acid method) | 47 | 39 |

If, however, mineral acid is added to these solutions pursuant to the invention in such amounts, so that the pH of the solutions lies within the range of 1 to 4.5, the following concentration ranges can be achieved when the same fat mixture is used.

METHOD OF THE INVENTION

| Quaternization with | Mineral Acid | pH | Solids Content | Betaine Content |
| --- | --- | --- | --- | --- |
| ClCH$_2$COONa | HCl | 4.5 | 51–53 | 41–43 |
| ClCH$_2$COOH/KOH | HCl | 4.4 | 53–54 | 43–44 |
| ClCH$_2$COOH/KOH | HCl | 3.3 | 53–54 | 43–44 |
| ClCH$_2$COOH/KOH | HCl | 1.4 | 61 | 46–47 |
| ClCH$_2$COOH/KOH | H$_3$PO$_4$ | 4.0 | 54–55 | 43–44 |
| ClCH$_2$COOH/KOH | H$_2$SO$_4$ | 2.5–3.0 | 54 | 43–44 |

The Table shows that it is possible with this embodiment of the inventive method to prepare solutions, which are still flowable and the betaine content of which is at least 10% higher than that of corresponding solutions of the state of the art.

The following Table shows the effect of the composition of the fatty acid mixture, used in the preparation of the fatty acid amidamine of formula I, on the limiting concentration of the still flowable betaine solutions, the pH of which is about 3.

| Fatty Acid or Fatty Acid Mixture | Maximum Solids Content in % by weight |
| --- | --- |
| C$_8$ fatty acid | 60 to 61 |
| C$_{10}$ fatty acid | 53 |
| C$_{12}$ fatty acid | 44 |
| C$_{14}$ fatty acid | 38 |
| Coconut fatty acid, stripped | 43 |
| Coconut fatty acid, hydrogenated | 54 |
| Coconut fatty acid, hydrogenated + palm kernel fatty acid, hydrogenated, in a 1:1 mixture | 54 |
| as above, but in a 3:1 mixture | 54 |

It can also be seen from the Table that it is possible to prepare solutions of a higher concentration when mixtures of fatty acids are used than when pure fatty acids are used, the number of carbon atoms of which corresponds to the average number of carbon atoms of the fatty acid mixture.

A preferred embodiment of the inventive method is characterized in that 1 to 5% by weight, based on the solution, of water-soluble nonionic surfactants are added to the reaction mixture before or during the quaternization or to the betaine solution obtained and before its pH is adjusted to a value of 1 to 4.5. If necessary, the acidic solution of the betaines, so obtained, is adjusted to a pH of ≧5 to 9 by addition of alkaline solution.

The processing properties of the betaine solution, obtained pursuant to the invention, are improved severalfold by the addition of the nonionic surfactants, especially in that the opacities and striations, occasionally present in the solution, are solubilized, so that the solutions become optically clear. The solutions do not segregate any opacities even on prolonged standing. They exhibit outstanding cold stability. At the same time, the viscosity of the solution is lowered even further.

As water-soluble nonionic surfactants, the polyoxyalkylene derivatives of fatty alcohols, fatty acids or partial esters of fatty acids and multihydric alcohols are preferred. Example sof such preferred compounds are the polyoxyethylene ethers of fatty alcohols with 8 to 18 carbon atoms. These fatty alcohols may be saturated or unsaturated and substituted or unsubstituted. Examples of such fatty alcohols are lauryl, stearyl and oleyl alcohol. Furthermore, the polyoxyethylene esters of fatty acids are suitable as nonionic surfactants. Examples of suitable fatty acids are lauric, stearic, oleic and castor oil fatty acid, as well as fatty acid mixtures obtained from natural fats. Moreover, the ethoxylated fatty acid mono- and diglycerides and the corresponding ethoxylated esters of sorbitol and fatty acids are suitable. The HLB values of these nonionic surfactants should range especially from 14 to 20.

The alkylpolyglucosides and their alkoxyltion products are also suitable as nonionic surfactants. Especially suitable are alkylglucosides, the alkyl groups of which have 8 to 12 carbon atoms.

The nonionic surfactants may be added to the reaction mixture for the synthesis of the betaines. In this case, however, only those surfactants are usable, which are not split (saponified) under the reaction conditions, such as the polyoxyethylene ethers of the fatty alcohols. Preferably, the surfactants are, however, added to the betaine solution obtained. However, the addition must take place before the acidifcation of the betaine solution pursuant to the inventive method.

In general, the addition of 1 to 5% by weight, based on the solution, suffices to achieve the desired effect. The addition of the nonionic surfactants does not interfere with the further use of the betaine solutions, since the betaine solutions generally are compounded with nonionic surfactants when used for the preparation of shampoos or shower gels. The addition of 1 to 5% by weight of nonionic surfactants is therefore to be understood as only a minimum amount to ensure the desired cold stability and the low viscosity of the solutions. It is, of course, also possible to add larger amounts of nonionic surfactants to the betaine solutions.

Surprisingly, it has been ascertained that an acidic betaine solution, which contains nonionic surfactants and which has been prepared pursuant to the invention, can be adjusted without danger of gelling to a pH of $\geq 5$ to 7. This is of importance, especially with regard to the reduced corrosiveness of the solutions. If a betaine solution, prepared pursuant to the invention and devoid of nonionic surfactants, is neutralized, gelling takes place, as the following Table shows:

The solution contains 53 to 54% by weight solids, of which 43 to 44% by weight is betaine based on hydrogenated coconut fatty acid. It is adjusted to a pH of 3.3 with HCl. A solution without nonionic surfactant is compared with a solution with 4.1% by weight of ethoxylated sorbitan monolaurate:

|  | Without Surfactant | With Surfactant |
|---|---|---|
| Viscosity | 1,000 mPas at 25° C. | 600 mPas at 25° C. |
| Appearance | slightly cloudy, striations | clear |
| Cold Stability | <16° C. gelatinous | clear to 0° C. |
| After Neutralization | gelling | liquid up to pH 9 |

The inventive method thus permits the preparation of liquid pumpable and meterable betaine solutions, which are based, for example on coconut fatty acid and have a betaine content of at least 37 to about 50% by weight.

The solutions, prepared pursuant to the invention, can readily be diluted and do not form any gel structures on dilution. The betaine solutions can be made up in the usual way. Making up is understood to be the adjustment of the concentration to the desired value and optionally the addition of dyes, fragrances, other skin-care substances and/or thickeners.

The inventive method is described in greater detail in the following examples, it being understood that these examples re given by way of illustration and not by way of limitation.

EXAMPLE 1

(Comparison, not of the Invention)

In to a 1-L 4-neck flask with stirrer, thermometer and reflux condenser are weighed 300 g of fatty acid amidamine of formula II (in which $R^1$ is the alkyl portion of a fatty acid mixture $R^1COOH$ obtained from hydrogenated coconut fat, $R^2$ and $R^3$ are methyl groups, $x=3$, $y=2$), 128 g of sodium chloroacetate and 590 g of water. The reaction mixture is heated to a temperature of 95° to 98° C. After a reaction period of 10 to 12 hours, the content of unreacted fatty acid amidamine is less than 2% by weight. A clear, homogeneous, liquid product, with a pH of 5 and weighing 1.018 g, is obtained.

Solids Content: 42% by weight
Betaine Content: 36% by weight

The solution obtained is concentrated by evaporation. When a solids content of 43 to 44% by weight is reached, a solid gel is formed.

EXAMPLE 2

(Comparison, not of the Invention)

In an apparatus like that of Example 1, 103 g of monochloroacetic acid is dissolved in 458 g of water at 60° to 70° C. The fatty acid amidamine named in Example 1 (300 g) is melted at 30° to 40° C. and added to the solution of the monochloroacetic acid. An exothermic reaction takes place. The solution obtained is cooled to 75° to 80° C. At this temperature, a solution of 44 g of NaOH in 44 g of water is allowed to run in over a period of 1 hour. The temperature is raised to 95° to 98° C. and maintained there for 4 to 6 hours to complete the reaction. At the end of this time, the fatty acid amidamine content has fallen to <2% by weight. A clear, homogeneous liquid product (949 g) with a pH of 5 is obtained.

Solids Content: 44% by weight
Betaine Content: 38% by weight

The solution obtained is concentrated by evaporation. When a solids content of 46% by weight is reached, a solid gel is formed.

EXAMPLE 3

(Comparison, not of the Invention)

In an apparatus like that of Example 1, 103 g of monochloroacetic acid is dissolved in 420 g of water at 60° to 70° C. The fatty acid amidamine named in Example 1 (300 g) is melted at 30° to 40° C. and added to the solution of the monochloracetic acid. An exothermic reaction takes place. The solution obtained is cooled to 75° to 80° C. At this temperature, a solution of 73 g of 85% by weight KOH in 50 g of water is allowed to run in over a period of 1 hour. The temperature is raised to 95° to 98° C. and maintained there for 4 to 6 hours to complete the reaction. At the end of this time, the fatty acid amidamine content has fallen to <2% by weight. A clear, homogeneous liquid product (949 g) with a pH of 5 is obtained.

Solids Content: 47% by weight
Betaine Content: 39% by weight

The solution obtained is concentrated by evaporation. When a solids content of 48% by weight is reached, a solid gel is formed.

EXAMPLE 4

(Of the invention)

The method of Example 3 is repeated. At the end of the reaction, nitrogen is passed over the solution obtained and the reflux condenser is removed. Aqueous HCl (15 g of a 36% solution) is added. Water is subsequently removed until the solids content is determined to be 53 to 54% by weight. A slightly cloudy, liquid solution (827 g) is obtained.
 Solids Content: 54% by weight
 Betaine Content: 44% by weight
 pH: 4.4

EXAMPLE 5

(Of the Invention)

The method of Example 4 is repeated. However, 30 g of 36% aqueous HCl is added. The solution is evaporated to a solids content of 54%. A cloudy, liquid solution (842 g) is obtained.
 Solids Content: 54% by weight
 Betaine Content: 44% by weight
 pH: 3.3

EXAMPLE 6

(Of the Invention)

The method of Example 4 is repeated. However, 100 g of 36% aqueous HCl is added and the solution produced is concentrated to a solids content of 61% by weight, 790 g of a viscous but pourable, cloudy solution being obtained.
 Solids Content: 61% by weight
 Betaine Content: 46 to 47% by weight
 pH: 1.4

EXAMPLE 7

(Of the Invention)

The method of Example 4 is repeated. However, 10 g of 85% aqueous phosphoric acid is added. The solution produced is concentrated to a solids content of 54% by weight, 840 g of a cloudy, liquid solution being obtained.
 Solids Content: 54% by weight
 Betaine Content: 44% by weight
 pH: 4

EXAMPLE 8

(Of the Invention)

The method of Example 4 is repeated. However, 10 g of 98% sulfuric acid is added. the solution produced is concentrated to a solids content of 54% by weight, 840 g of a cloudy, liquid solution being obtained.
 Solids Content: 54% by weight
 Betaine Content: 43 to 44% by weight
 pH: 2.5 to 3

EXAMPLE 9

(Of the Invention)

In an apparatus like that of Example 1, 103 g of monochloroacetic acid is dissolved in 400 g of water at 60° to 70° C. The fatty acid amidamine (300 g), used in Example 1, is melted at 30° to 40° C. and added to the solution. An exothermic reaction takes place. The solution obtained is cooled to 75° to 80° C., at which temperature a solution of 73 g of KOH (85%) in 50 g of water is allowed to run in over a period of one hour.

To this reaction mixture are added 100 g of melted fatty acid amidamine and 34 g of monochloroacetic acid. A solution of 24 g of KOH (85%) in 17 g of water is allowed to run in at a temperature of 75° to 80° C. The temperature of the solution is then increased to 95° to 98° C. After 4 to 6 hours, the free fatty acid amidamine content has fallen to <2% by weight, whereupon 40 g of 36% aqueous HCl is added and the product is allowed to cool. A clear, homogeneous, liquid product (1,140 g) with a pH of 3.3 is obtained.
 Solids Content: 54% by weight
 Betaine Content: 44% by weight
 pH: 3.3

EXAMPLE 10

(Of the Invention)

The method of Example 5 is repeated. However, 50 g of a 70% by weight aqueous polyoxyethylene sorbitan monolaurate solution is added before the acidification. Subsequently, 30 g of 36% by weight HCl is added as in Example 5. The solution, warmed slightly to 30° to 35° C., is stirred until a clear solution is formed. The solution obtained is then treated with such amounts of a 47% by weight aqueous KOH solution, that a pH of 4 to 5 results. A comparison with the product of Example 5 reveals the following:

|  | Without Surfactant | With Surfactant |
| --- | --- | --- |
| Viscosity | 1,000 mPas at 25° C. | 600 mPas at 25° C. |
| Appearance | slightly cloudy, striations | clear |
| Cold Stability After Neutralization | <16° C. gelatinous gelling | clear liquid to 0° C. liquid to pH 9 |

EXAMPLE 11

The method of Example 5 is repeated. However, the fatty acid amidamines used for the preparation of the betaines are derived from different fatty acids or fatty acid mixtures. The concentrations are determined at which the solutions obtained, which have a pH of about 3, are still liquid.

| Fatty Acid or Fatty Acid Mixture | Maximum Solids Content in % by weight |
| --- | --- |
| $C_8$ fatty acid | 60 to 61 |
| $C_{10}$ fatty acid | 53 |
| $C_{12}$ fatty acid | 44 |
| $C_{14}$ fatty acid | 38 |
| Coconut fatty acid, stripped | 43 |
| Coconut fatty acid, hydrogenated | 54 |
| Coconut fatty acid, hydrogenated + palm kernel fatty acid, hydrogenated, in a 1:1 mixture | 54 |
| as above, but in a 3:1 mixture | 54 |

EXAMPLE 12

In an apparatus like that of Example 1, 103 g of monochloroacetic acid is dissolved in 400 g of water at 60° to 70° C. The fatty acid amidamine named in Example 1 (300 g) is melted at 30° to 40° C. and added to the solution. An exothermic reaction takes place. The solution obtained is cooled to 75° to 80° C. At this temperature, a solution of 73 g of of 85% by weight KOH in 50 g of water is allowed to run in over a period of 1 hour.

To this reaction mixture are added 100 g of molten fatty acid amidamine, 34 g of monochloroacetic acid and 57 g of polyoxyethylene lauryl ether. A solution of 24 g KOH (85%) in 17 g of water is allowed to run in at 75° to 80° C. The temperature of the solution is then raised to 95° to 98° C. After 4 to 6 hours, the content of free fatty acid amidamine has fallen to <2% by weight. Aqueous HCl (36%, 40 g) is added and the temperature is allowed to fall. A clear, homogeneous, liquid product, weighing 1,200 g and having a pH of 3.3, is obtained.

Solids Content: 55% by weight
Betaine Content: 44% by weight
pH: 4

The solution obtained is neutralized with aqueous KOH solution. The solution remains liquid and clear. It can be cooled to 5° C. without loss of flowability and without becoming opalescent.

I claim:

1. In a method for the preparation of flowable aqueous solutions of betaines of the general formula

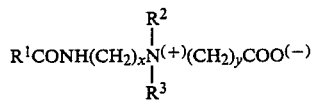

wherein
$R^1$ is the alkyl portion of a fatty acid with 6 to 18 carbon atoms,
$R^2$, $R^3$ are the same or different and represent alkyl with 1 to 4 carbon atoms
x is 2 or 3 and
y is 1, 2 or 3
by quaternization of fatty acid amides

wherein $R^1$, $R^2$, $R^3$ and x have the above meaning, with ω-halogenalkylcarboxylic acids $X(CH_2)_yCOOY$ or their salts (X=halogen, Y=a hydrogen, alkali or ammonium ion) in aqueous solution at elevated temperatures, the improvement which comprises that after the quaternization, mineral acid is added to the aqueous betaine solution thus obtained, said mineral acid being added in an amount sufficient to obtain a pH of the solution of about between 1 to 4.5.

2. The improvement of claim 1, wherein said mineral acid is added to the solution while it is still hot from the quaternization reaction.

3. The improvement of claim 1, wherein the concentration of the betaine solution is adjusted for a predetermined value by evaporation of water from the solution, said mineral acid being added to the solution before or after said adjustment of the concentration.

4. The improvement of claim 1, wherein between about 1 to 5 percent by weight, calculated on the betaine solution, of a water-soluble nonionic surfactant is added to the reaction mixture before or during the quaternization reaction.

5. The improvement of claim 4, wherein said surfactant is a polyoxyethylene ether of a fatty alcohol.

6. The improvement of claim 1, wherein between about 1 to 5 percent by weight, calculated on the betaine solution, of a water-soluble, nonionic surfactant is added to the betaine solution before the addition of the mineral acid.

7. The improvement of claim 6, wherein said water-soluble nonionic surfactant is a polyoxyethylene derivative of fatty alcohols, fatty acids, or partial esters of fatty acids and multihydric alcohols with an HLB value of 14 to 20.

8. The improvement of claim 4, wherein the pH of the acidic betaine solution is ultimately adjusted to a value of between about ≧5 to 9 by the addition of an alkaline solution.

9. The improvement of claim 6, wherein the pH of the acidic betaine solution is ultimately adjusted to a value of between about ≧5 to 9 by the addition of an alkaline solution.

10. The improvement of claim 3, wherein the concentration of the solution is adjusted to a solids content of about between 43 to 65 percent by weight and a betaine content of between 37 to 55 percent by weight.

11. The improvement of claim 1, wherein the mineral acid is hydrochloric acid, sulfuric acid of phosphoric acid.

12. The product obtained by the method of claim 1 or 10.

13. The product obtained by the method of claim 4 or 6.

14. The product obtained by the method of claim 8 or 9.

* * * * *